United States Patent
Chen et al.

(12)

(10) Patent No.: US 6,258,567 B1
(45) Date of Patent: Jul. 10, 2001

(54) PREPARATION OF $^{13}$C/$^{15}$N-LABELED OLIGOMERS USING THE POLYMERASE CHAIN REACTION

(75) Inventors: Xian Chen, Los Alamos; Goutam Gupta; E. Morton Bradbury, both of Santa Fe, all of NM (US)

(73) Assignee: The Regents of the University of California, Los Alamos, NM (US)

( * ) Notice: Subject to any disclaimer, the term of this patent is extended or adjusted under 35 U.S.C. 154(b) by 0 days.

(21) Appl. No.: 09/322,899

(22) Filed: May 29, 1999

(51) Int. Cl.$^7$ .............................. C12P 19/34; C12N 1/20; C07M 21/00
(52) U.S. Cl. ................... 435/91.1; 435/91.2; 435/252.3; 435/325; 536/25.32
(58) Field of Search .............................. 435/91.2, 252.3, 435/325, 91.1; 536/25.32

(56) References Cited

PUBLICATIONS

Zon et al. The Polymerase Chain Reaction Colony Miniprep, Bio Techniques, vol. 7(7), p. 696–8, 1989.*
Sambrook et al. Molecular Cloning: a laboratory manual, second edition, p. 14.14–14.17.*
Daniel P. Zimmer et al., "NMR of Enzymatically Synthesized Uniformly 13C15N–Labeled Oligonucleotides," Proc. Natl. Acad. Sci., U.S.A. 92, 3091 (1995).
John M. Louis et al., "Preparation of Uniformly Isotope–Labeled DNA Oligonucleotides of NMR Spectroscopy," J. Bio. Chem. 273, 2374 (1998).
Carmen C. Robinett et al., "In Vivo Localization of DNA Sequences and Visualization of Large–Scale Chromatin Organization Using Lac Operator/Repressor Recognition," J. Cell Biol. 135, 1685 (1996).

* cited by examiner

*Primary Examiner*—Stephanie W. Zitomer
*Assistant Examiner*—Joyce Tung
(74) *Attorney, Agent, or Firm*—Samuel M. Freund (57) ABSTRACT

Preparation of $^{13}$C/$^{15}$N-labeled DNA oligomers using the polymerase chain reaction (PCR). A PCR based method for uniform ($^{13}$C/$^{15}$N)-labeling of DNA duplexes is described. Multiple copies of a blunt-ended duplex are cloned into a plasmid, each copy containing the sequence of interest and restriction Hinc II sequences at both the 5' and 3' ends. PCR using bi-directional primers and uniformly $^{13}$C/$^{15}$N-labeled dNTP precursors generates labeled DNA duplexes containing multiple copies of the sequence of interest. Twenty-four cycles of PCR, followed by restriction and purification, gave the uniformly $^{13}$C/$^{15}$N-labeled duplex sequence with a 30% yield. Such labeled duplexes find significant applications in multinuclear magnetic resonance spectroscopy.

6 Claims, 5 Drawing Sheets

PREPARATION OF $^{13}$C/$^{15}$N-LABELED OLIGOMERS USING THE POLYMERASE CHAIN REACTION

The invention was made with government support under Contract No. W-7405-ENG-36 awarded by the U.S. Department of Energy to the Regents of The University of California. The government has certain rights in the invention.

FIELD OF THE INVENTION

The present invention relates generally to a method for uniformly labeling double-stranded DNA with stable isotopes of carbon and nitrogen and, more particularly, to the use of the polymerase chain reaction with labeled deoxynucleotide triphosphate precursors and Taq DNA polymerase to prepare uniformly labeled DNA duplexes.

BACKGROUND OF THE INVENTION

Since the advent of well-developed and standard techniques for the syntheses of uniformly $^{13}$C/$^{15}$N-labeled proteins and ribonucleic acids (RNA), multinuclear magnetic resonance (NMR) spectroscopy has been routinely applied for the determination of their structures. By comparison, the determination of DNA structures by multidimensional NMR is infrequent primarily due to the lack of economic and efficient techniques for the synthesis of uniformly $^{13}$C/$^{15}$N-labeled DNA molecules. The availability of $^{13}$C/$^{15}$N-labeling allows resolution and sequential assignment of spin-systems belonging to individual nucleotides in a long DNA duplex which, in turn, results in the generation of a large set of distance constraints that are essential for determining high-resolution structures. The generation of NMR spectra of uniformly labeled DNA enables the delineation of the structures of DNA complexes with specific proteins and the identification of conformational changes in DNA upon protein binding.

In principle, labeled DNA molecules can be chemically or enzymatically synthesized. However, the preparation of such oligodeoxynucleotides (DNA) by chemical synthesis is uncommon because the generation of uniformly $^{13}$C/$^{15}$N-labeled, chemically protected mononucleotides required for phosphoramidite polymerization is costly, inefficient and technically challenging, since such species are not available commercially. DNA labeling by enzymatic methods was introduced by D. P. Zimmer et al. in "NMR Of Enzymatically Synthesized Uniformly $^{13}$C/$^{15}$N-Labeled Oligonucleotides," Proc. Natl. Acad. Sci., U.S.A. 92, 3091 (1995) and includes template-directed synthesis using Klenow DNA polymerase and a mixture of labeled deoxynucleoside triphosphate precursors (dNTPs). However, control of the extent of chain elongation is difficult; therefore, for preparation of labeled DNA having a desired length, hairpin templates must be designed such that the single-stranded overhang in the stem controls the length of the newly synthesized DNA strand. Alternatively, an RNA primer may be used in the enzymatic synthesis of labeled DNA having a defined length. In both procedures, uniformly $^{13}$C/$^{15}$N-labeled DNA duplexes are obtained by adding equimolar quantities of two complementary strands made from two different templates. Inherent in these methods, then, is a step in which the newly synthesized labeled strand is separated from an unlabeled template. This is achieved using denaturing gel electrophoresis, followed be elution of the DNA from the gel matrix. Poor yields of labeled DNA and residual polyacryamide contamination are concerns for NMR applications.

The Polymerase Chain Reaction (PCR) has recently been used to prepare uniformly isotope-labeled DNA oligonucleotides. In "Preparation Of Uniformly Isotope-Labeled DNA Oligonucleotides For NMR Spectroscopy," by John M. Louis et al. J. Bio. Chem. 273, 2374 (1998), the chain extension is based upon self-priming which leads to synthesis of multiple copies of the sequence of interest having flanking restriction sites. Self-priming PCR works well only for GC-rich DNA strands, but not for AT-rich strands, since for AT-rich DNA strands, the melting temperature is significantly lowered and the accuracy of amplification deteriorates. Additionally, Louis et al. reports that some of the oligonucleotides cannot be cleaved to monomers, so that an additional chromatography step is necessary to remove the approximately 10% of unwanted dimeric material present after the DNA amplification.

Accordingly, it is an object of the present invention to provide a general method for preparing uniformly $^{13}$C/$^{15}$N-labeled single- or double-stranded oligodeoxynucleotides with high efficiency and accuracy.

Another object of the present invention is to provide a general method for preparing uniformly $^{13}$C/$^{15}$N-labeled single- or double-stranded oligodeoxynucleotides, without the necessity for complex purification steps.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, the method for the preparing $^{13}$C/$^{15}$N-labeled oligomers of this invention includes: attaching one Hinc II moiety to each end of the oligomer to be labeled; inserting the oligomer thus formed into a plasmid at a Hinc II site therein; amplifying the oligomer using PCR with the plasmid-oligomer as a template, chosen distinct upper and lower primers, and $^{13}$C/$^{15}$N-enriched dNTPs as precursors, such that a $^{13}$C/$^{15}$N-enriched oligomer strand is produced having an overall length determined by the primers selected and the length of the oligomer; and digesting the Hinc II moieties, whereby the desired $^{13}$C/$^{15}$N-labeled oligomer is generated.

It is preferred that the plasmid is inserted into cells which are grown to produce recombinant clones containing inserts of the oligomer before using PCR to amplify the plasmid-oligomer template.

Preferably also, the generated $^{13}$C/$^{15}$N-enriched oligomer produced is purified and then massively amplified using PCR with the chosen upper and lower primers and $^{13}$C/$^{15}$N-enriched dNTPs as precursors, before the Hinc II moieties are digested.

Benefits and advantages of the present invention include an efficient and general procedure for preparing labeled oligomers without the requirement of significant purification steps.

BRIEF DESCRIPTION OF THE DRAWINGS

The accompanying drawings, which are incorporated in and form a part of the specification, illustrate the embodi- In the drawings:

FIGS. 1a–e schematically describe the basic steps of the polymerase chain reaction (PCR)-based method of the present invention for preparing uniformly $^{13}C/^{15}N$-labeled DNA duplexes, where

FIG. 2a shows the gel electrophoresis results for a portion of the PCR products with different concentrations of $^{13}C/^{15}N$-labeled dNTPs, while FIG. 2b shows the gel electrophoresis results for a portion of the purified, labeled PCR products after Hinc II digestion.

FIGS. 3a–c show the NMR spectra of the $^{13}C/^{15}N$-labeled duplex, d(G1-A2-C3-A4-T5-T6-A7-T8-G9-T10-T11-T12-A13-G14-T15-C16)•d(G17-A18-C19-T20-A21-A22-A23-C24-A25-T26-A17-A28-T29-G30-T31-C32) recorded in water at 5° C., where

DETAILED DESCRIPTION

Briefly, the present invention includes a method based upon the polymerase chain reaction (PCR) for large-scale synthesis of uniformly $^{13}C/^{15}N$-labeled DNA duplexes which does not require separation of the labeled DNA from the unlabeled one. In addition, the product to template ratio is $2^n$:1 for n PCR cycles rather than 1:1 for present template-based methods. The following steps are included in the synthesis: (1) ligation of the monomeric target sequence (TS) oligonucleotides with one Hinc II moeity separating each TS oligonucleotide into an oligonucleotide polymer containing a plurality of TS oligonucleotides; (2) insertion of the oligonucleotide polymer into a pUC19 plasmid at a Hinc II site therein; (3).PCR amplification using pUC19-TS as a template and $^{13}C/^{15}N$-enriched dNTPs as precursors; and (4) Hinc II digestion and purification of the labeled target sequence. Two-dimensional heteronuclear magnetic resonance spectra illustrate the uniformity of the $^{13}C/^{15}N$-labeling of DNA by helping to resolve resonance overlap. Additional detailed studies of the high resolution structure of the subject duplex derived from three-dimensional nuclear Overhauser effect spectroscopy (NOESY) data will enable confirmation of whether this yeast replication origin sequence is bent. High-resolution structure of the yeast replication origin is of biological significance since the structure determines the mechanism of the initiation of replication in which specific protein factors are involved. It has been postulated that this replication origin sequence is intrinsically bent which may have important implications in the binding of proteins to this replication origin.

Having generally described the invention the following EXAMPLE provides more detailed information.

EXAMPLE

Figure 1:
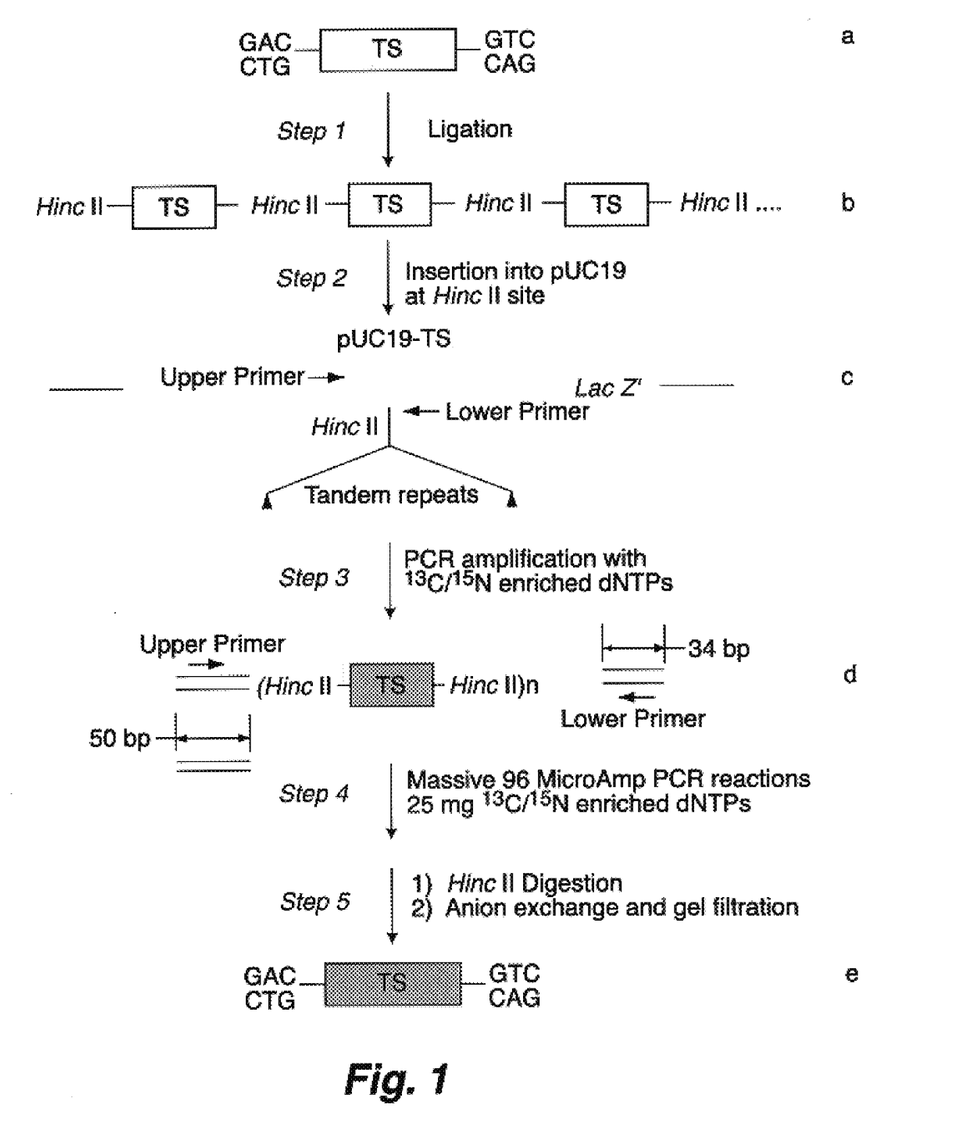
FIG. 1a illustrates the oligonucleotide-containing target sequence (TS) having two flanking Hinc II sites.
FIG. 1b illustrates the ligation product of the target sequence containing a chosen number of copies of the TS.
FIG. 1c illustrates a portion of the pUC19-TS plasmid containing primer annealing sites used to amplify the tandem repeat TS inserted thereinto at a Hinc II site.
FIG. 1d illustrates the PCR amplification of the product derived from the cloned plasmids.
FIG. 1e illustrates the $^{13}C/^{15}N$-labeled oligonucleotide containing the TS after digestion of the Hinc II and purification thereof.

Reference will now be made in detail to the present preferred embodiment of the invention, an example of which are illustrated in the accompanying drawings. Turning to the Figures, FIGS. 1a and 1b are schematic representation of the preparation of the polymerase chain reaction (PCR) template of a recombinant DNA plasmid containing the target sequence (TS) for which labeling is desired. The TS was synthesized with a blunt-end Hinc II site at both the 5' and 3' ends (Step 1 of FIG. 1a). After phosphorylation, monomers of the TS were ligated to produce multiple copies of the TS each separated by a Hinc II site, plus one Hinc II site at each end of the ligation product. The ligation product (FIG. 1b) was sized on an 0.8% agarose gel. Bands corresponding to the largest number of the tandem repeats were extracted from the gel and purified.

The purified oligomer was then inserted at the Hinc II site of pUC19 (Step 2 of FIG. 1b). After transformation into E.coli XL-2 blue cells, the resulting cells were plated onto solid LB media containing 2% X-gal and 1 mM IPTG on the surface. The recombinant clones containing inserts of tandem repeats were selected by their characteristic white color. The number of TSs, n, was determined by ABI DNA sequencing for each individual recombinant plasmid. The recombinant, pUC19-TS, (FIG. 1c) with the maximum repeat number of TS (n=19) was selected for the PCR template and further purified on 0.5% agarose gel.

Amplification using PCR with the consequent ($^{13}C/^{15}N$)-labeling of the target sequence is shown in Step 3 of FIG. 1d. Optimized PCR primers were selected by computer program that gave melting temperatures of 54° C. for the primer-attached duplexes. The upper primer, 5' AAACGACGGC-CAGTGMT 3', SEQ ID NO. 2, is located 50 base-pairs away from the Hinc II site, and the lower primer, 5' ACCATGAT-TACGCCMGC 3', SEQ ID NO. 3, is located 34 base-pairs away from the Hinc II site.

The plasmid (pUC19-TS) DNA (100 ng per 100 $\mu$l) is used as the template with labeled dNTPs as precursors. After reaction, the reaction mixture was loaded on a 1.0% agarose gel, and the labeled product was extracted from the gel and purified. This labeled product contained primer annealing sites and multiple copies of the TS that was subsequently used for massive PCR amplification (Step 4 of FIG. 1d).

PCR reactions were carried out in 100 $\mu$l batches in a commercially available PCR apparatus. The 100 $\mu$l PCR batches typically contained the following: 10 $\mu$l of 10×PCR buffer (1×100 $\mu$l); 2 $\mu$l of 25 mM $MgCl_2$ (2.0 mM); 5 $\mu$l of 20 $\mu$m upper primer (5.9 $\mu$g/ml, 1 $\mu$M); 5 $\mu$l of 20 $\mu$m lower primer (5.9 $\mu$g/ml, 1 $\mu$M); 100 ng of $^{13}C/^{15}N$-labeled template (1 $\mu$g/ml); 0.5 unit of Taq DNA polymerase (5 units/ml); and 200 $\mu$l (20 nmoles, 6.6 $\mu$g) of each $^{13}C/^{15}N$-labeled dNTP.

Figure 2:
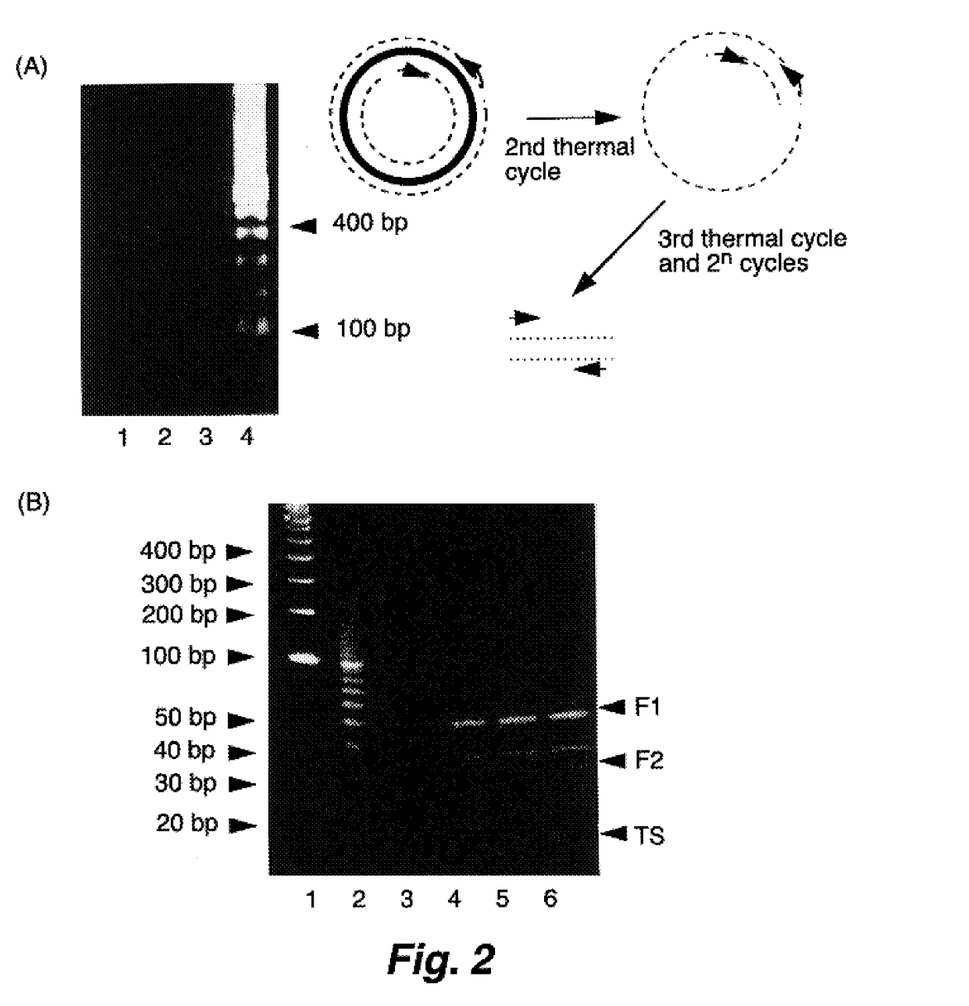

Each reaction tube was first pre-denatured at 96° C. for 30 seconds before the following thermal cycle: denaturation at 96° C. for 15 s, annealing at 50° C. for 30 s, and extension for 1 min. at 72° C. As shown in FIG. 2a, the extension reaction of the upper primer will stop at the position of the 3' end of the lower primer while the extension of the lower primer will be terminated at the 5' end of the upper primer. Also shown in FIG. 2a is a 1% agrose gel electrophoresis of a portion of PCR products with different concentrations of $^{13}C^{15}N$-labeled dNTPs when pUC19-TS is used as a template: Lane 1, 5 mM; Lane 2, 10 mM; and Lane 3, 20 mM. Lane 4 shows various double-stranded markers. The PCR products are about 400 base-pairs in size and contain 19 copies of the labeled TS (16 mer) oligodeoxynucleotide with unlabeled primers at both ends. About 20% labeled dNTPs were incorporated. The PCR products from each tube (about 0.4 mg PCR product per plate) were combined to obtain the final product. FIG. 2b is 4-20% gradient polyacrylamide gel electrophoresis of a portion of the purified, labeled PCR products after Hinc II digestion: F1 is the flanking fragment from the upper primer to the Hinc II site; F2 is the flanking fragment from the lower primer to the Hinc II site; and TS is the labeled target sequence (16 mer): Lanes 1 and 2, double-stranded markers; Lane 3, partially digested PCR products; and Lanes 4, 5, and 6, complete Hinc II digestion of the PCR products.

The products were then purified to remove unincorporated $^{13}C/^{15}N$-dNTP, unreacted primers, and the Taq DNA polymerase. The unincorporated dNTPs were recovered on a Q-Sepharose anion exchange column.

The labeled TS was isolated by Hinc II restriction and purified by anion exchange and gel filtration columns (Step 5 of FIG. 1d) as follows. After initial digestion of the PCR product of Step 4 of FIG. 1d with Hinc II (1 unit for 1 µg at 37° C. for 1 hour), 0.5 unit of fresh enzyme per mg of DNA was added and the mixture incubated for an additional 1 hour to ensure a complete Hinc II digestion. The digestion product was checked by polyacrylamide gel electrophoresis (PAGE). The digested product was loaded on a Q-Sepharose anion exchange (1.0×10 cm) column. Five column volumes of 1 mM phosphate buffer (pH=7.0) with 0.1 mM EDTA were used to prewash the column to remove non-DNA impurities. The column was then washed with 1 mM phosphate buffer (pH=7.0) with a 0-1.5 M NaCl gradient at a flow rate of 1 m/min. Five ml fractions were collected in each tube and the target DNA sequence was eluted at approximately 160 mM NaCl.

The semipurified sample was loaded on a Sephacryl S-200 (2.5×50 cm) column with a DNA exclusion limit of 30 base-pairs. This allows separation of the TS from other digested DNA fragments. The column was subsequently eluted with 1 mM phosphate buffer (pH=7.0) containing 0.1 mM EDTA at a flow rate of 1.0 ml per min. collecting 3 ml fractions. An aliquot from each tube was examined by PAGE to locate the target oligonucleotide which eluted at approximately 160 mM NaCl. Fractions containing TS were pooled and concentrated to 5 ml by ultrafiltration. After n thermal cycles of PCR, $2^n$ copies of the target sequence are produced.

The present DNA amplification procedure is more efficient than the well-known template-driven method in which the target sequence is produced at a 1:1 ratio with the template DNA. The labeled dNTPs are incorporated as efficiently as the naturally occurring dNTPs by PCR since the enrichment of the stable ($^{13}C/^{15}N$) isotopes has no effect on PCR. Although Taq polymerase transfers a non-template nucleotide adduct to the 3'-end of each strand of the PCR products due to its terminal deoxynucleotidyl transferase activity, this difficulty is eliminated by introducing a restriction site at both ends of the target sequence. In addition, the length of the labeled DNA of particular sequence is controlled by the restriction site.

The length of the PCR product extended from upper and lower primers is dictated by the following mechanism. In the first cycle, single-stranded DNA is derived from the strands of the parent plasmid with a nick at 5'-hydroxyl end of each primer. In the PCR cycles which follow, each primer is annealed at its complementary strand and the extension is stopped at the nick position; that is, as is shown in FIG. 2a, the extension reaction of the upper primer stops at the 3' end of the lower primer while the extension of the lower primer is terminated at the 5' end of the upper primer. After n cycles of PCR, $2^n$ copies of "d" are produced from the pUC19-TS template containing 19 copies of the TS.

The PCR product prepared according to the teachings of the present invention contains 19 copies of the target sequence. The cutoff sizes of flanking sequences from both primer ends are 50 base-pairs and 34 base-pairs, respectively. The flanking regions are also labeled with $^{13}C/^{15}N$, i.e., (i.e., 50+34−18×2=48) base pairs. The ratio of the labeled target sequence to the labeled flanking region is calculated as: number of monomer TS, n, times the length of TS divided by 48. Therefore, the efficiency of labeling the TS increases with larger numbers of tandem repeats. For n=19, percentage of labeled target sequence in undigested PCR product will be 19×16/19×16+48=87%.

The labeled PCR template shown in FIG. 1d has been produced on a large scale. All the nucleotides incorporated in this template are labeled except for the primer ends. The PCR amplification of the DNA oligomer from this template gives labeled products with 99% enrichment of $^{13}C/^{15}N$-isotopes (that is, the same as the enrichment of the dNTPs). Hinc II digestion of the PCR product and subsequent purification result in the 16-mer duplex suitable for NMR studies.

In the EXAMPLE, 19 copies of the TS were inserted into the plasmid. C.C. Robineft et al. in J. Cell Biol. 135, 1685 (1996) has shown that 256 direct repeats of the lac operator can be inserted in a plasmid. Incorporation of a high copy number of the target sequence will enhance the efficiency of the present PCR method in which the number of copies of the sequence of interest is precisely controlled. The actual sequence and the length of the sequence of interest determines the maximum number of copies that can be inserted in the plasmid. The larger the number of copies the higher is the efficiency of this method for double-stranded and single-stranded DNA.

In order to circumvent the problem of low DNA concentration and poor signal-to-noise ratio, ($^{13}C$-$^{1}H$) NMR measurements were performed experiments on a 720 MHz spectrometer. A susceptibility matched NMR tube that having microliter sample volume was used for all measurements. One mM DNA sample in buffered solution of 10 mM sodium phosphate (pH=7.0) and 150 mM NaCl was used for all NMR measurements. Hydrogen ($^{1}H$) chemical shifts were measured with reference to 3,3,3-trimethylsilylpropionate as an internal standard. $^{15}N$ chemical shifts were measured with reference to $K^{15}NO_3$ and converted into the primary reference of nitromethane in accordance with standard protocols. The $^{15}N$ excitation was centered at 276.06 ppm from saturated $KNO_3$. The $^{13}C$ chemical shifts were measured from tetramethylsilane (TMS) as a secondary reference. The $^{13}C$ excitation was centered at 100 ppm from TMS. 100 ppm for $^{13}C$ occurs at the decoupler offset of 0 Hz in $H_2O$ or $D_2O$. Two-dimensional heteronuclear ($^{15}N$-$^{1}H$ and $^{13}C$-$^{1}H$) single and multiple quantum coherence (HSQC and HMQC) experiments were performed on the labeled 16-mer duplex. In all the experiments, water suppression was achieved via WATERGATE pulse scheme.

Figure 3A:
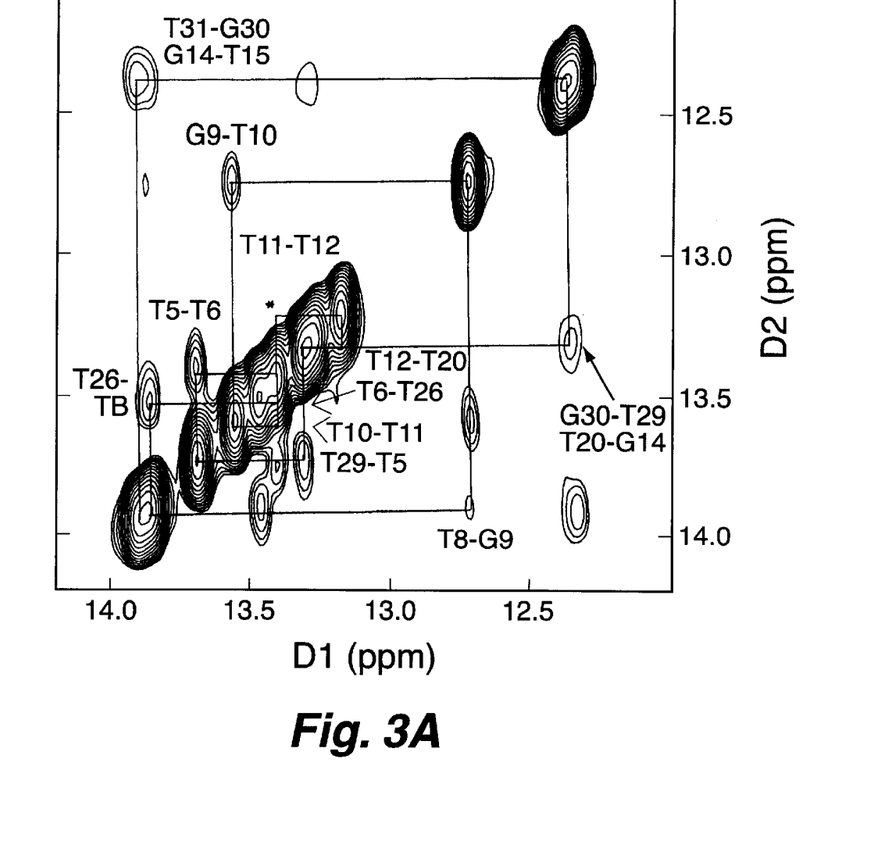
FIG. 3a is a 150 ms [$^1H$-$^1H$] NOESY spectrum showing the imino—imino sequential connectivities.

FIG. 3a shows the imino—imino 500 MHz NOESY connectivities of the duplex, d(G1-A2-C3-A4-T5-T6-A7-

Figure 3B:
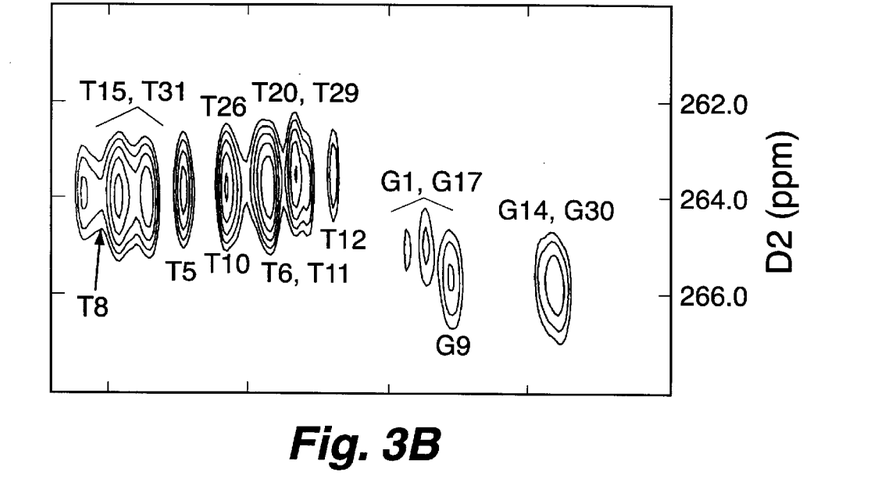
FIG. 3b is a selected region of the ($^{15}N$-$^1H$) HSQC spectrum showing the imino resonances.
Figure 3C:
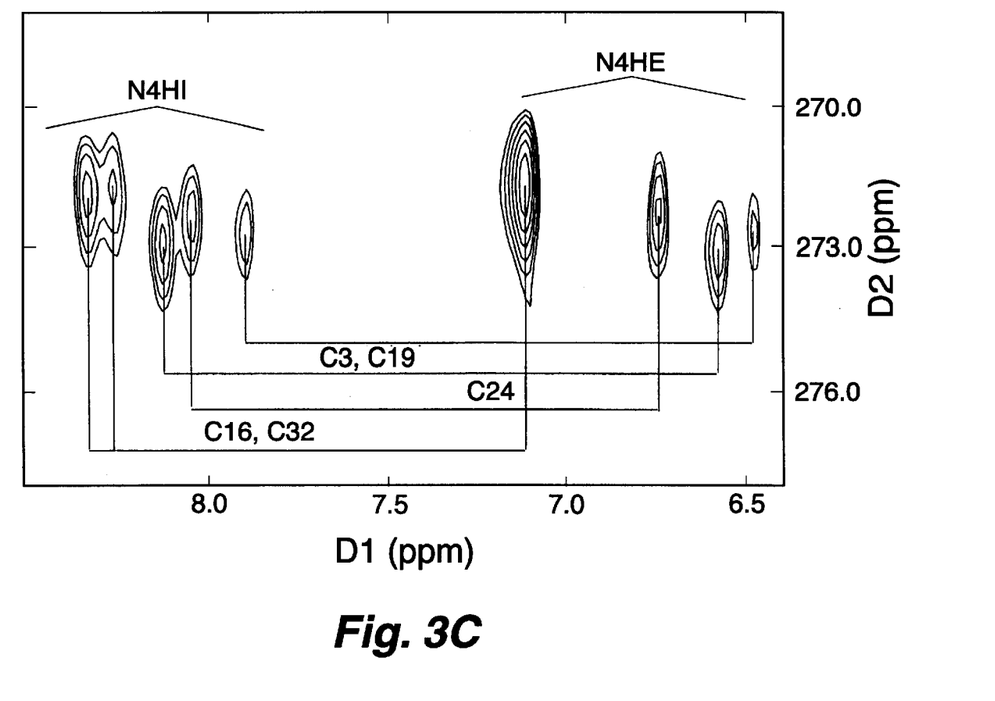
FIG. 3c is a selected region of the ($^{15}N$-$^1H$) HSQC spectrum showing the cytosine amino resonances.

T8-G9-T10-T11-T12-A13-G14-T15-C16)•d(G17-A18-C19-T20-A21-A22-A23-C24-A25-T26-A17-A28-T29-G30-T31-C32). Since they are well resolved, the sequential connectivity can easily be established among the imino protons. The $^{15}$N chemical shifts of the imino nitrogens are obtained from the ($^{15}$N-$^{1}$H) HSQC cross-section shown in FIG. 3B. Note that the 15N resonances of the imino nitrogens are poorly resolved except that the G•C pairs are downfield-shifted relative to the A•T pairs. In contrast, the five amino pairs from the five G•C pairs display better dispersion in the $^{15}$N dimension (see FIG. 3C).

Figure 4A:
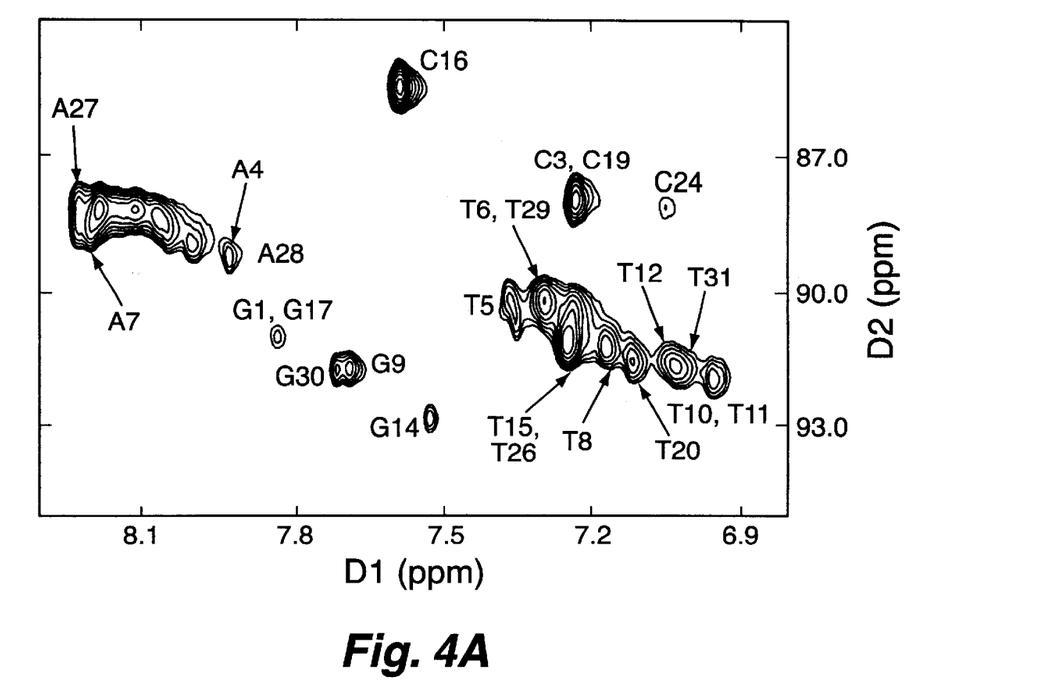
FIGS. 4a and 4b show selected Regions of the $^{13}C$-$^1H$ HMQC spectrum of the duplex: d(G1-A2-C3-A4-T5-T6-A7-T8-G9-T10-T11-T12-A13-G14-T15-C16)•d(G17-A18-C19-T20-A21-A22-A23-C24-A25-T26-A17-A28-T29-G30-T31-C32) recorded in $D_2O$ at 25° C., where FIG. 4a demonstrates the $C_8/C_6$—$H_8/H_6$ correlations, and FIG. 4b demonstrates the $C_2$—$H_2$ correlations for adenines.
Figure 4B:
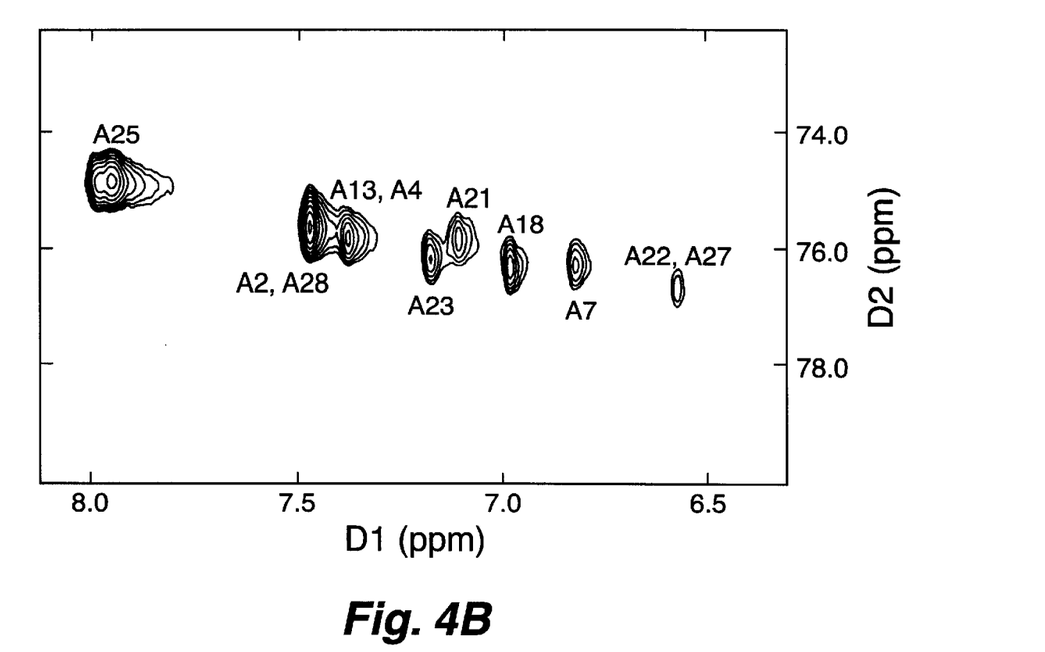

The overlap of the non-exchangeable base protons (H8/H6/H2) is removed by ($^{13}$C-$^{1}$H) HMQC experiments at 720 MHz. FIGS. 4*a* and 4*b* show such correlations involving C8/C6-H8/H6 and C2-H2. Note that the H8 protons of adenines and guanines are clustered as two different groups and so are the H6s of cytosines and thymines. The H2s of adenines are located at 20 ppm higher field than the corresponding H8s.

The power of NMR spectroscopy with labeled DNA is clearly demonstrated in FIGS. 4*a* and 4*b* which show that the resonance overlap in the $^{1}$H dimension is removed by $^{13}$C labeling. As is also shown in FIGS. 4*a* and 4*b*, resolution of the base (H8/H6/H2) protons belonging to 32 different nucleotides will allow identifications of their interactions with other base and sugar protons. This data set produces a large number of inter-proton distance constraints that are needed to obtain a high resolution structure of a DNA complex of this length. For the ARS-A sequence, DNA labeling is particularly useful in determining the interactions involving H2s of adenines which are helpful in identifying intrinsic DNA bending. The bending of ARS-A may be important in defining the nucleosome boundary in the yeast replication origin since the ARS elements (i.e., B1, B2, B3, and A) should all be free of nucleosomes before the start of replication.

The foregoing description of the invention has been presented for purposes of illustration and description and is not intended to be exhaustive or to limit the invention to the precise form disclosed, and obviously many modifications and variations are possible in light of the above teaching. For example, although only the synthesis of uniformly labeled DNA duplexes is discussed, the method of the present invention can readily be extended to the synthesis of uniformly labeled single-stranded DNA. The modification of the present method would involve a thiol-group attachment at the 5' end of one primer that is extended to produce the strand of interest. After isolation, the fragment (FIG. 1*d*) would be treated with exonuclease. The thiol-modified strand would be protected whereas the other strand would be digested. The thiol-modified single strand would then be annealed with GTC_GAC which would produce Hinc II digestion sites (marked _) on the single strand at regular intervals. Therefore, Hinc II treatment of the thiol-modified strand with subsequent purification would create the single-stranded sequence of interest plus three nucleotide fragments at each end. It is not clear how the method of Louis et al., supra, which is based on self-priming, can be extended to the synthesis of labeled single strands. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for preparing uniformly $^{13}$C/$^{15}$N-labeled oligomers, which comprises the steps of:
   (a) attaching one Hinc II restriction moiety to each end of the oligomer to be labeled forming thereby a first oligomer;
   (b) inserting said first oligomer into a plasmid having a Hinc II moiety located therein at the location of the Hinc II moiety;
   (c) using the polymerase chain reaction (PCR) with chosen distinct upper and lower primers, with $^{13}$C/$^{15}$N-labeled deoxynucleoside triphosphate precursors (dNTPs) as precursors, to amplify a second oligomer which includes the first oligomer and part of the plasmid as a template, the second oligomer having an overall length determined by the primers selected and the length of the first oligomer, whereby a $^{13}$C/$^{15}$N-labeled second oligomer is produced; and
   (d) digesting the Hinc II moieties from said second oligomer, whereby the desired $^{13}$C/$^{15}$N-labeled oligomer is generated.

2. The method for preparing uniformly $^{13}$C/$^{15}$N-labeled oligomers as described in claim 1, wherein the plasmid is pUC19, the upper primer is 5' AAACGACGGCCAGTGMT 3', SEQ ID No. 2, and the lower primer, 5' ACCATGATTACGCCMGC 3', SEQ ID No. 3.

3. The method for preparing uniformly $^{13}$C/$^{15}$N-labeled oligomers as described in claim 2, further comprising the steps of purifying said $^{13}$C/$^{15}$N-labeled second oligomer produced from said step of using PCR to amplify said second oligomer with chosen distinct upper and lower primers, and said $^{13}$C/$^{15}$N-labeled dNTPs as precursors, and massively amplifying said purified said $^{13}$C/$^{15}$N-labeled second oligomer using PCR with the chosen upper and lower primers and said $^{13}$C/$^{15}$N-labeled dNTPs as precursors, before said step of digesting the Hinc II moieties from said second oligomer.

4. The method for preparing uniformly $^{13}$C/$^{15}$N-labeled oligomers as described in claim 1 further comprising the steps of inserting said plasmid into cells, and growing the cells produced thereby, whereby recombinant clones containing inserts of said first oligomer are generated before said step of using PCR to amplify said second oligomer.

5. The method for preparing uniformly $^{13}$C/$^{15}$N-labeled oligomers as described in claim 4, wherein the plasmid is pUC19, the cells include *E. coli* XL2 cells, the upper primer is 5' AAACGACGGCCAGTGAAT 3', SEQ ID NO. 2, and the lower primer, 5' ACCATGATTACGCCMGC 3', SEQ ID NO. 3.

6. The method for preparing uniformly labeled $^{13}$C/$^{15}$N-labeled oligomers as described in claim 1 wherein said first oligomer to be labeled is formed by ligating additional first oligomer to be labeled to form an oligonucleotide polymer containing a chosen number of the oligomer to be labeled with one Hinc II moiety separating each oligomer to be labeled and one Hinc II moiety at each end of the oligonucleotide polymer thus formed.

* * * * *

SEQUENCE LISTING

```
<160> NUMBER OF SEQ ID NOS: 3

<210> SEQ ID NO 1
<211> LENGTH: 16
<212> TYPE: DNA
<213> ORGANISM: Artificial Sequence
<220> FEATURE:
<223> OTHER INFORMATION: Description of Artificial Sequence:Target
      Sequence

<400> SEQUENCE: 1
gacattatgt ttagtc                                                    16

<210> SEQ ID NO 2
<211> LENGTH: 18
<212> TYPE: DNA
<213> ORGANISM: pUC19

<400> SEQUENCE: 2
aaacgacggc cagtgaat                                                  18

<210> SEQ ID NO 3
<211> LENGTH: 17
<212> TYPE: DNA
<213> ORGANISM: pUC19

<400> SEQUENCE: 3
accatgatta cgccagc                                                   17
```